(12) United States Patent
Chan et al.

(10) Patent No.: US 9,150,506 B2
(45) Date of Patent: Oct. 6, 2015

(54) SULFONATED AROMATIC COMPOUNDS

(71) Applicant: E I DU PONT DE NEMOURS AND COMPANY, Wilmington, DE (US)

(72) Inventors: Justin W. Chan, Wilmington, DE (US); Michael W Cobb, Wilmington, DE (US); Sharlene Renee Williams, Wilmington, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 13/915,704

(22) Filed: Jun. 12, 2013

(65) Prior Publication Data
US 2013/0338376 A1    Dec. 19, 2013

Related U.S. Application Data

(60) Provisional application No. 61/660,123, filed on Jun. 15, 2012.

(51) Int. Cl.
C07C 309/60    (2006.01)
C07D 327/08    (2006.01)
C07C 309/44    (2006.01)
C08G 63/672    (2006.01)

(52) U.S. Cl.
CPC ............. *C07C 309/60* (2013.01); *C07C 309/44* (2013.01); *C07D 327/08* (2013.01); *C08G 63/672* (2013.01)

(58) Field of Classification Search
CPC ... C07C 309/44; C07C 309/60; C07D 327/08
See application file for complete search history.

(56) References Cited

PUBLICATIONS

Jouanneau et al. (Journal of Polymer Science Part A: Polymer Chemistry 2010, vol. 48 (8);pp. 1732-1742—published online on Mar. 8, 2010).*
STN Registry in the Chemical Abstracts Service (Dec. 25, 2004 and Nov. 16, 1984).*
U.S. Appl. No. 13/915,696, filed Jun. 12, 2013.
U.S. Appl. No. 13/915,711, filed Jun. 12, 2013.

* cited by examiner

*Primary Examiner* — Valerie Rodriguez-Garcia

(57) ABSTRACT

Described are sulfonated aromatic compounds and methods of making said compounds. The compounds are useful as monomers in a variety of polymers such as polyamides and polyesters, and can impart flame resistant properties.

7 Claims, No Drawings

SULFONATED AROMATIC COMPOUNDS

This application claims the benefit of priority of U.S. Provisional Application No. 61/660,123 filed on Jun. 15, 2012, the entirety of which is herein incorporated by reference.

FIELD OF THE INVENTION

The invention is directed to sulfonated aromatic compounds and methods of making said compounds.

BACKGROUND

Workers that can be exposed to flames, high temperatures, and/or electrical arcs and the like, need protective clothing and articles made from thermally resistant fabrics. Any increase in the effectiveness of these protective articles, or any increase in the comfort, durability, and dyeability of these articles while maintaining protection performance, is welcomed.

Polyamide and polyester polymers have unique properties and are useful in many fields, for example high performance fibers, such as flame retardant fibers. One method to improve flammability is to prepare sulfonated polymers. These methods have included the use of sulfonated monomers and post-sulfonation.

There is a need for compounds that can be used to prepare polymers such as polyamide and polyester with a high degree of sulfonation, leading to improved properties such as increased flame retardancy and dyeability.

SUMMARY

Disclosed within is a compound of Formula (I) or Formula (II):

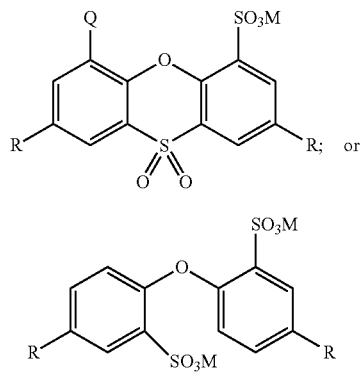

wherein
Q is H or $SO_3M$;
M is one or more cations; and
each R is independently $CO_2H$, $CO_2R^1$, $COCl$, or $CONHNH_2$, or salts thereof, where $R^1$ is an 1-5 carbon alkyl group.

DETAILED DESCRIPTION

Described herein is a compound of Formula (I) or Formula (II)

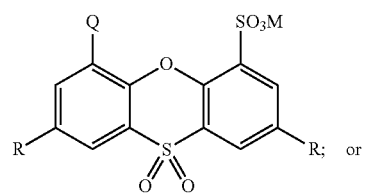

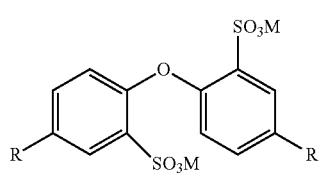

wherein Q is H or $SO_3M$; M is one or more cations; and each R is independently $CO_2H$, $CO_2R^1$, $COCl$, or $CONHNH_2$, or salts thereof, where $R^1$ is an 1-5 carbon alkyl group.

M is typically a monovalent cation such as H, Li, Na, K, or $NH_4$, or mixture thereof, but is typically H. $R^1$ is an 1-5 carbon alkyl group but is typically ethyl or methyl and more typically methyl.

The compound can be present as the closed ring structure of Formula I, the open ring structure of Formula II, or a mixture of both. Additionally, when Formula I is present, Q can be either H or $SO_3M$, or a mixture.

In one embodiment the two R substituents are the same; in another embodiment the can differ two R substituents are different from each other.

Various embodiment of the compound are shown below but are not limited to these embodiments:

Acids

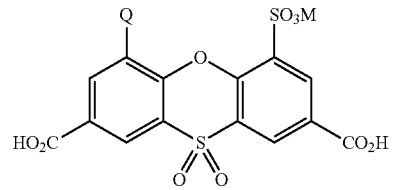

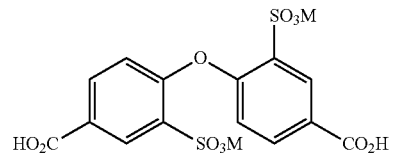

Monoesters

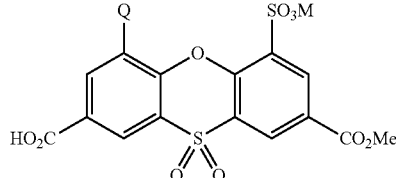

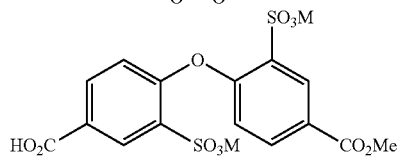

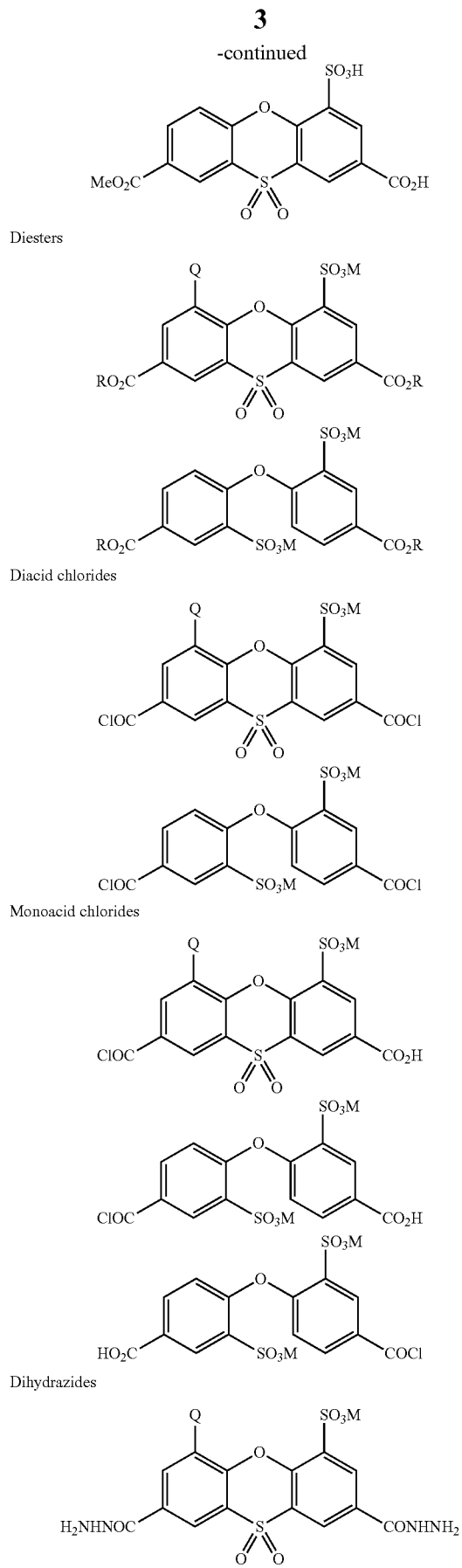

Diesters

Diacid chlorides

Monoacid chlorides

Dihydrazides

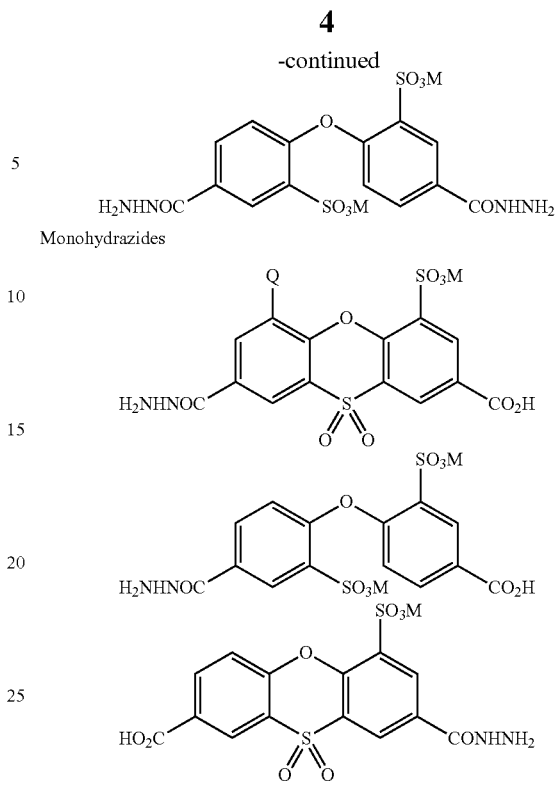

Monohydrazides

The compounds disclosed herein are useful as monomers and endcappers for polymers including but are not limited to polyoxadiazoles, polyesters, polyamides, aramids, and for materials such as fibers and coatings. They are particularly useful for flame retardant materials.

The sulfonated aromatic acids can be prepared by any method known in the art. One method is via the sulfonation of the corresponding aromatic acids. One suitable synthesis is disclosed in co-pending U.S. Pat. Appl. 61/423,616. As therein described, the sulfonated aromatic diacids are made by adding a oleum to an aromatic acid, such as 4,4'-oxybis (benzoic acid), in the presence of heat. They may be purified by recrystallization or other methods known to those skilled in the art.

The esters can be prepared using any known in the art, such as esterification with the corresponding alcohol with a catalyst present. They may be purified by recrystallization or other methods known to those skilled in the art.

The sulfonated diacid chlorides can be prepared by combining sulfonated aromatic diacids and thionyl chloride or oxalyl chloride in the presence of dioxane, heating the reaction mixture to about 60° C. for several hours, and then cooling the mixture to room temperature. The excess thionyl chloride can then be removed, and the desired sulfonated aromatic diacid chlorides can be further isolated by additional distillation. More than one sulfonated aromatic diacid chloride can be present in the reaction mixture, and each can be isolated via methods such as distillation, recrystallization or chromatography. To analyze for reaction completion, LC-MS can be utilized, where the acid chloride is reacted with an amine, such as butylamine. This is done to prevent the diacid chloride from undergoing hydrolysis in water back to the starting material.

The sulfonated aromatic dihydrazines can be made by combining the sulfonated aromatic diesters and hydrazine monohydrate to form a reaction mixture, heating the reaction mixture to reflux in a solvent such as methanol and then adding the reaction mixture to water to precipitate out the sulfonated aromatic dihydrazines. They may be purified by recrystallization or other methods known to those skilled in the art.

EXAMPLES

Unless otherwise stated, the examples were all prepared using the following procedures. Ratios of reagents are given as mole ratios. para-Phenylene diamine (PPD), meta-phenylene diamine (MPD), and 1,3-propanediol were obtained from E. I. du Pont de Nemours and Company, Wilmington, Del. Terephthalic acid (TPA), isophthalic acid (IPA), 4,4'-oxybis(benzoic acid) (OBBA), 1,4-dioxane, thionyl chloride, oxalyl chloride, butylamine, calcium chloride, N-methylpyrrolidone (NMP), triphenylphosphite, dimethylterephthalate, Tyzor® TPT (titanium (IV) isopropoxide), sulfuric acid, hydrazine monohydrate, hexamethylene diamine (HMD), and pyridine were obtained from Sigma-Aldrich®. Methanol (MeOH) was obtained from BDH. Acetonitrile was obtained from EMD Chemicals.

Examples 1-8

Sulfonylated 4,4'-oxybis(benzoic acid)

A 40 mL vial containing a magnetic stir bar was charged with 4,4'-oxybis(benzoic acid) (6.0 g) and 30% oleum (39.6 g). The mixture was heated in a 130° C. hot block for 3 days. Samples (1 mL) of the resulting clear brown solution were then quenched with water and vortexed to mix. The precipitated solids were filtered and sparingly washed with ice water. The remaining solid was predominately the monosulfonated sulfone product and the aqueous filtrate predominately contained the disulfonated sulfone. $^1$H NMR spectrum and LC/MS were performed and indicate that the desired sulfonated and sulfonylated products were formed.

A saturated solution of the monosulfonated sulfone product was prepared in water-$d_2$ containing a trace of sodium 3-trimethylsilylpropionate-$d_4$ as a chemical shift referent. The solution was inserted in a NMR probe and heated to 60° C. to ensure dissolution. A series of NMR two dimensional correlation experiments were performed to elucidate the structure of the material. These experiments permitted assignment of the $^1$H resonances of the primary product, 4-sulfophenoxathiine-2,8-dicarboxylic acid 10,10-dioxide. The $^1$H assignments (in ppm relative to chemical shift referent at 0.00 ppm) are shown in the following below.

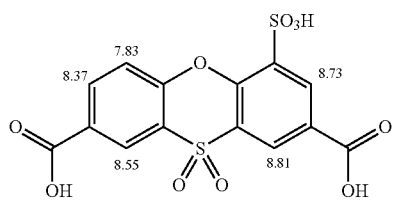 [SMILES: O=C(O)c1ccc2c(c1)S(=O)(=O)c1cc(C(=O)O)cc(S(=O)(=O)O)c1O2]

General Polyamide Polymerization Procedure

Unless otherwise specified, the following general polymerization procedure was used in each example while varying the ratio of the carboxylic acid monomers as specified in Table 1. The molar ratio of diamine to dicarboxylic acid was always 1:1. In a drybox, a 20 mL vial with a stirbar was charged with the carboxylic acids indicated in the table (1.200 mmol), diamines (1.200 mmol), $CaCl_2$ (0.208 g), NMP (2 mL), triphenyl phosphite (1.2 mL), and pyridine (0.400 mL). The solids did not appear to dissolve at room temperature. The mixture was placed in a 120° C. hot block. After approximately 15 minutes, the solution was clear yellow with a small amount of solids at the bottom of the vial. After approximately 25 minutes, the reaction was a viscous yellow gel with some solids at the bottom of the vial. The solids were believed to be $CaCl_2$. The temperature was increased to 140° C. for 1 hour. The viscous yellow solution flowed very slowly at room temperature. MeOH (15 mL) was added to the vial and stirred. A white polymer precipitated. The precipitation was repeated and the material was washed with hot water and MeOH. The solid was then dried in a vacuum oven for 18 hours at 125° C.

The results are shown in Table 1 below.

TABLE 1

| EX | Diamine | TPA | IPA | S-OBBA | Mn | Mw | Mw/Mn |
|---|---|---|---|---|---|---|---|
| 1[1] | MPD | 0 | 100 | 0 | 14300 | 34500 | 2.41 |
| 2 | MPD | 0 | 80 | 20 | 11400 | 27800 | 2.43 |
| 3 | MPD | 0 | 50 | 50 | 7500 | 19000 | 2.53 |
| 4 | PPD | 0 | 0 | 100 | 10100 | 26000 | 2.59 |
| 5 | MPD | 0 | 90 | 10 | 22000 | 72100 | 3.28 |
| 6[1] | HMD | 100 | 0 | 0 | 5500 | 14000 | 2.55 |
| 7 | HMD | 80 | 0 | 20 | 4000 | 13000 | 3.25 |

[1]Comparative example
HMD = Hexamethylene diamine
PPD = paraphenylene diamine
MPD = metaphenylene diamine
TPA = terephthalic acid
IPA = isophthalic acid
S-OBBA = sulfonated OBBA

Example 8

Acid Chloride Synthesis

In a drybox, two 20 mL vials with stirbars were charged with sulfonated OBBA (0.5005 g, 1.250 mmol) and dioxane. This was allowed to stir at 60° C. for 15 min. The solid did not dissolve. The vial was removed from the heat and allowed to cool to room temperature. Oxalyl chloride (0.2433 mL, 2.8754 mmol) was added to one vial and thionyl chloride (0.2102 mL, 2.8818 mmol) was added to another vial. The vials were then allowed to heat to 60° C. for several hours. Samples were taken for LC-MS analysis by first reacting the acid chloride with butylamine and analyzing that product. This was done because the diacid chloride would hydrolyze in water to the starting material.

Example 9

Synthesis and Proof of Structure of Sulfonylated 4,4'-oxybis(benzoic acid) dimethyl ester A 200 mL round-bottom flask containing a magnetic stir bar was charged with sulfonated 4,4'-oxybis(benzoic acid) (6.0 g), methanol, and sulfuric acid (39.6 g). The solids dissolved at room temperature into a clear solution. The solution was placed in a 90° C. oil bath for 24 hours. The solvent was removed via rotary evaporation to yield a yellow solid, which was then repeatedly washed with acetonitrile and water. The solid was then recrystallized from methanol. The solid was dried in a vacuum oven for 18 hours at 125° C. The structure was confirmed via LC-MS, $^1$H NMR, and X-ray crystallography. The $^1$H assignments (in ppm relative to chemical shift referent at 0.00 ppm) are shown below.

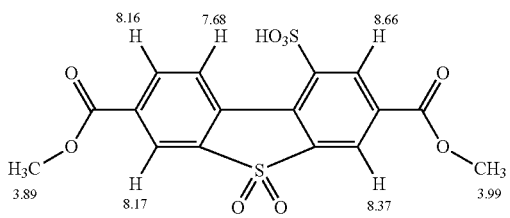

Example 10

Dihydrazide Synthesis

A 100 mL round bottom flask equipped with a reflux condenser and stirbar was charged with hydrazine monohydrate (1.337 g, 26.708 mmol) and methanol (4 mL). A suspension containing the sulfonated OBBA dimethylester from Example 9 and methanol (40 mL) was slowly added. The solids dissolved, and the solution was allowed to reflux while stirring for 22 hours.

Example 11

Polyester Containing Sulfonated OBBA Dimethylester

Dimethylterephthalate (50.44 g, 0.26 mol) and sulfonated OBBA dimethylester (11.14 g, 0.026 mol) from Example 9 were charged to a 250 mL three-necked round bottom flask. An overhead stirrer and a distillation condenser were attached. The reaction mass was kept under a static $N_2$ atmosphere. The contents were degassed once by evacuating down to 100 mtorr and refilling back with $N_2$ gas. To this, 1,3-propanediol (39.18 g, 0.51 mol) was added. The contents were degassed again twice. At the second degas step the overhead stirrer was turned on at a speed of 3 rpm. The flask was immersed in a preheated metal bath set at 160° C. The stirrer speed was slowly increased to 180 rpm and the solids were allowed to completely melt at 160° C. 210 μL of catalyst Tyzor® TPT was added under a $N_2$ blanket. The temperature was increased to 210° C. The system was maintained at 210° C. for 60 minutes to distill off most of the methanol produced. The temperature was increased to 250° C. and was held constant for 30 minutes. The nitrogen flush was closed off and vacuum ramp was started. After 17 min, the vacuum reached a value of 67 mtorr. The reaction was maintained under vacuum for approximately 65 min. The polymer obtained was a brown solid that was glass-like and brittle. The $^1$H NMR revealed additional peaks that indicated that the monomer from Example 9 was incorporated.

Example 10

Comparative Example

Preparation of Homopolymer from dimethylterephthalate and 1,3-propanediol

Dimethylterephthalate (150 g, 0.77 mol), and 1,3-propanediol (105.9 g, 1.39 mol) were charged to an oven-dried 500 mL three necked round bottom flask equipped with an overhead stirrer and a distillation condenser. The reactants were stirred under a nitrogen purge at a speed of 10 rpm while the condenser was kept at 23° C. The contents of the flask were degassed three times by evacuating down to 500 mTorr and refilling back to atmospheric pressure with $N_2$ gas. Tyzor® TPT catalyst (94 mg) was added after the first evacuation. Following the three degassing cycles, the flask was immersed into a preheated metal bath set at 160° C. The solids were allowed to completely melt at 160° C. for 20 minutes while the stirring speed was slowly increased to 180 rpm. The temperature was increased to 210° C. and was held at 210° C. for 90 minutes. After 90 minutes at 210° C., the temperature was increased to 250° C. after which the nitrogen purge was discontinued, and a vacuum ramp was started such that after about 60 minutes the vacuum reached a value of about 60 mTorr. After stirring (50-180 rpm) for an additional 3-4 hours the heat source was removed. The over-head stirrer was stopped. The vacuum was then turned off and the system purged with $N_2$ gas at atmospheric pressure. The product was allowed to cool to ambient temperature. The resulting polymer was white to off-white. $^1$H NMR indicated that the desired polymer structure had formed.

What is claimed is:

1. A compound of Formula (I) or Formula (II):

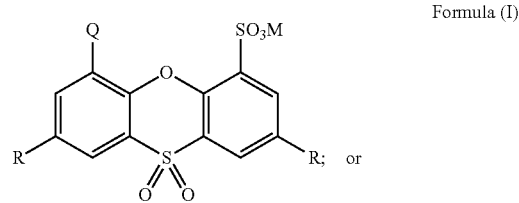

Formula (I)

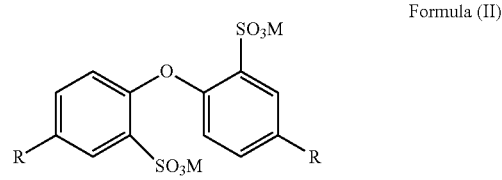

Formula (II)

wherein
Q is H or $SO_3M$;
M is a cation;
each R for Formula (I) is independently $CO_2H$, $CO_2R^1$, COCl, or $CONHNH_2$, or salts thereof, where $R^1$ is a 1-5 carbon alkyl group, linear or branched; and
each R for Formula (II) is independently COCl, or $CONHNH_2$, or salts thereof.

2. The compound of claim 1 wherein M is H, Li, Na, K or $NH_4$, or mixture thereof.

3. The compound of claim 1 wherein each R is the same.

4. The compound of claim 1 wherein said compound is of Formula (I) and wherein
Q is H or $SO_3M$;
M is a cation; and,
each R for Formula (I) is independently $CO_2H$, $CO_2R^1$, COCl, or $CONHNH_2$, or salts thereof, where $R^1$ is a 1-5 carbon alkyl group, linear or branched.

5. The compound of claim 4 wherein each R is $CO_2R^1$.

6. The compound of claim 5 wherein $R^1$ is methyl and Q is H.

7. The compound of claim 1 wherein said compound is of Formula (II) and wherein
Q is H or $SO_3M$;

M is a cation; and, each R for Formula (II) is independently COCl, or CONHNH$_2$, or salts thereof.

* * * * *